US012648687B2

(12) United States Patent
Wang et al.

(10) Patent No.: US 12,648,687 B2
(45) Date of Patent: Jun. 9, 2026

(54) METHOD AND APPARATUS OF ADAPTIVE LEAKAGE REDUCTION FOR PROCESSOR USED IN A CAPSULE ENDOSCOPE

(71) Applicant: CAPSOVISION, Inc., Saratoga, CA (US)

(72) Inventors: Kang-Huai Wang, Saratoga, CA (US); Chung-Ta Lee, Sunnyvale, CA (US)

(73) Assignee: CAPSOVISION INC., Saratoga, CA (US)

( * ) Notice: Subject to any disclaimer, the term of this patent is extended or adjusted under 35 U.S.C. 154(b) by 256 days.

(21) Appl. No.: 18/513,627

(22) Filed: Nov. 19, 2023

(65) Prior Publication Data

US 2025/0160634 A1     May 22, 2025

(51) Int. Cl.
*A61B 1/273*      (2006.01)
*A61B 1/00*       (2006.01)
*A61B 1/04*       (2006.01)
*A61B 1/06*       (2006.01)

(52) U.S. Cl.
CPC ........ *A61B 1/2733* (2013.01); *A61B 1/00009* (2013.01); *A61B 1/00097* (2022.02); *A61B 1/041* (2013.01); *A61B 1/0684* (2013.01); *A61B 1/2736* (2013.01)

(58) Field of Classification Search
CPC ... A61B 1/00036; A61B 1/00062; A61B 1/05; A61B 1/051; A61B 1/053; A61B 1/041; A61B 1/273; A61B 1/2733; A61B 1/2736; H04N 25/709; H10D 62/393
See application file for complete search history.

(56) References Cited

U.S. PATENT DOCUMENTS

| | | | | | |
|---|---|---|---|---|---|
| 5,068,719 A | * | 11/1991 | Tsuji | ................... | A61B 1/0669 600/101 |
| 2005/0022537 A1 | | 2/2005 | Lohn | | |
| 2008/0177136 A1 | * | 7/2008 | Wang | ................... | H04N 17/002 600/109 |
| 2011/0004059 A1 | * | 1/2011 | Arneson | .............. | A61B 1/0004 600/109 |
| 2011/0012594 A1 | * | 1/2011 | Kimura | .............. | A61B 1/00036 324/309 |
| 2014/0160259 A1 | * | 6/2014 | Blanquart | .............. | A61B 1/051 348/65 |
| 2015/0057548 A1 | * | 2/2015 | Kaufman | .............. | G01J 5/0893 600/473 |

(Continued)

*Primary Examiner* — Michael J Carey
*Assistant Examiner* — Stephen Floyd London
(74) *Attorney, Agent, or Firm* — Blairtech Solution LLC

(57)     ABSTRACT

Method and apparatus of imaging gastrointestinal tract by using a capsule endoscope According to this method, at least two operating states during a course of gastrointestinal examination using the capsule endoscope are determined, wherein said at least two operating states comprise a first operating state and a second operating state, and the capsule endoscope comprises one or more capsule processors equipped with a back bias control. In response to a current operating state being the first operating state or the second operating state, the current body biasing for said one or more capsule processors is set to a first body biasing or a second body biasing accordingly, wherein the first body biasing is different from the second body biasing. One or more images are captured using the current body biasing for said one or more capsule processors.

13 Claims, 3 Drawing Sheets

(56)     References Cited

U.S. PATENT DOCUMENTS

| | | | |
|---|---|---|---|
| 2019/0373197 A1* | 12/2019 | Harada | A61B 1/00009 |
| 2021/0076916 A1* | 3/2021 | Ming | A61B 1/045 |
| 2021/0185262 A1* | 6/2021 | Osawa | A61B 1/00006 |
| 2021/0400224 A1* | 12/2021 | Gocho | H04N 25/78 |
| 2023/0094219 A1* | 3/2023 | Takatsuka | H10F 39/803 |
| | | | 257/292 |

* cited by examiner 16 20 22 24 26

12

10 archival memory processing module battery

Output port

110

14

12

100

Vout

High-gain region

Vin

Oxide/
insulator
Oxide/
insulator
Bias voltage
contact
310
Oxide/
insulator
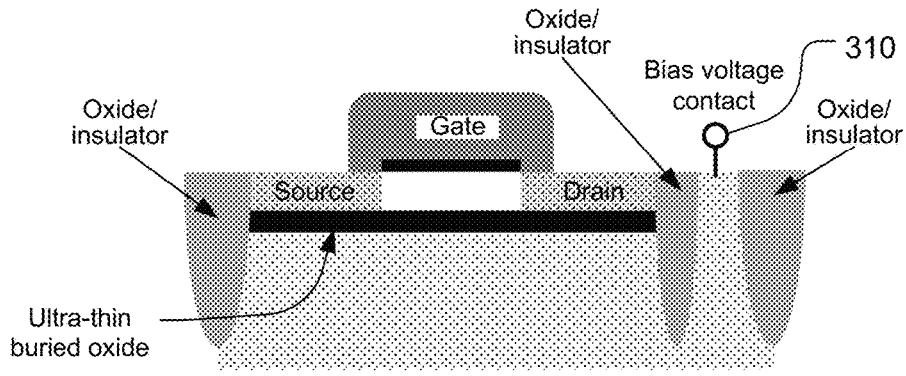
Gate
Source
Drain
Ultra-thin
buried oxide
*Fig. 3*
N-well contact
0V to +2V
nMOS
pMOS
P-well contact
0V to -2V
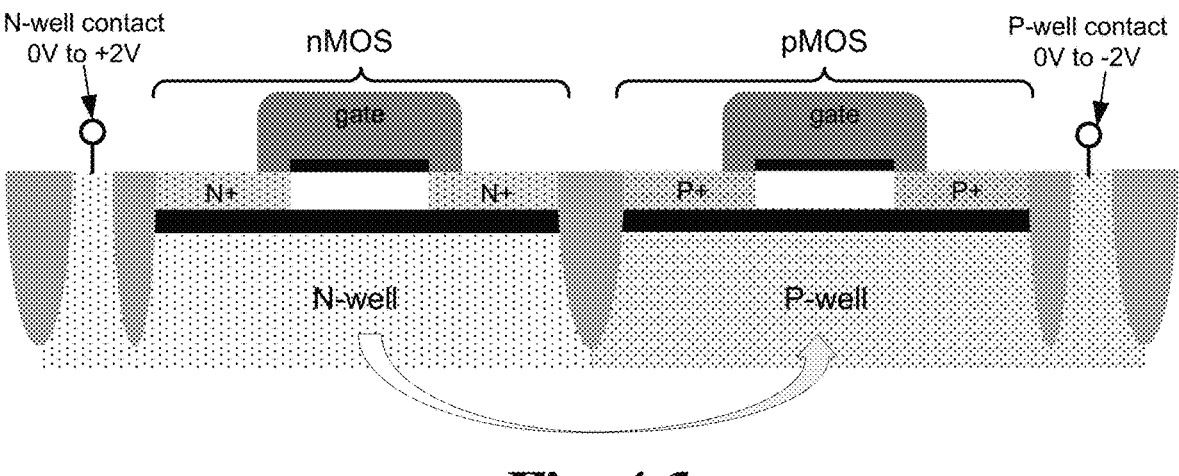
gate
gate
N+
N+
P+
P+
N-well
P-well
*Fig. 4A*
N-well contact
0V to -2V
nMOS
pMOS
P-well contact
0V to +2V
gate
gate
N+
N+
P+
P+
P-well
N-well
*Fig. 4B*

METHOD AND APPARATUS OF ADAPTIVE LEAKAGE REDUCTION FOR PROCESSOR USED IN A CAPSULE ENDOSCOPE

CROSS REFERENCE TO RELATED APPLICATIONS

The present invention is related to U.S. Pat. No. 7,495, 993, granted on Feb. 24, 2009. The U.S. patent is hereby incorporated by reference in its entirety.

FIELD OF THE INVENTION

The present invention is related to methods and apparatus of capturing in vivo gastrointestinal images. In particular, the present invention is related to techniques to extend the capsule endoscope life without impact on the performance.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot easily reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia.

An alternative in vivo image sensor that addresses many of these problems is the capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. Pat. No. 7,983,458, entitled "In Vivo Autonomous Camera with On-Board Data Storage or Digital Wireless Transmission in Regulatory Approved Band," granted on Jul. 19, 2011. This patent describes a capsule system using on-board storage such as semiconductor nonvolatile archival memory to store captured images. After the capsule passes from the body, it is retrieved. Capsule housing is opened and the images stored are transferred to a computer workstation for storage and analysis. For capsule images either received through wireless transmission or retrieved from on-board storage, the images will have to be displayed and examined by diagnostician to identify potential anomalies.

FIG. 1 illustrates an exemplary capsule system with on-board storage. The capsule device 110 includes illuminating system 12 and a camera that includes optical system 14 and image sensor 16. A semiconductor nonvolatile archival memory 20 may be provided to allow the images to be stored and later retrieved at a docking station outside the body, after the capsule is recovered. Capsule device 110 includes battery power supply 24 and an output port 26. Capsule device 110 may be propelled through the gastrointestinal (GI) tract by peristalsis.

Illuminating system 12 may be implemented by LEDs. In FIG. 1, the LEDs are located adjacent to the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls (100) on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. Processing module 22 may be used to provide processing required for the system such as image processing and video compression. The processing module may also provide needed system control such as to control the LEDs during image capture operation. The processing module may also be responsible for other functions such as managing image capture and coordinating image retrieval. While FIG. 1 illustrates a capsule endoscope with an archival memory to store captured images, the capsule endoscope may also be equipped with a wireless transmitter to transmit the captures to an external receiver.

After the capsule camera traveled through the GI tract and exits from the body, the capsule camera is retrieved and the images stored in the archival memory are read out through the output port. The received images are usually transferred to a base station for processing and for a diagnostician to examine. The accuracy as well as efficiency of diagnostics is most important. A diagnostician is expected to examine the images and correctly identify any anomaly.

The capsule device comprises one or more processors to perform various tasks, such as controlling lighting, capturing images, storing or transmitting images, etc., as required. In step with Moore's law, where the device feature sizes become increasingly smaller in each new generation of semiconductor processes, the operating voltage of the integrated circuits becomes lower. The lower voltage to deal with device punch through effect, hot electron, and oxide reliability comes in territory with the miniaturization of the transistors. It also has a very substantial advantage in reducing power consumption, due to the charge and discharge of a capacitance requiring less current since $CV=Q$ (C: capacitance and V: voltage, and Q: charge). Therefore, if V is lower, Q will be lower and lower current is required. The total energy on the other hand, which is important in greenhouse effect (for example the data center, search engine operation and the recent ChatGPT) or in battery operated system, is further dependent on operating voltage (energy=$QV=CV^2$). Furthermore, the heat generated will impact integrated circuit performance in the first place.

However, there is a competing factor creeping up that needs to be seriously considered. Take the example of an inverter, with transfer curve shown in FIG. 2. For it to be an effective switch, there must be a region of high gain in the transfer curve, where both P channel and N channel transistors are on, which in turns means operating voltage must be higher than $|VTN|+|VTP|$, where VTN and VTP are threshold voltages for n-channel and p-channel transistor's, respectively. Along with the dropping of the operating voltage, comes with the lower transistor threshold voltage by necessity. The transistor subthreshold current is an exponential function inversely proportional to the threshold voltage, measured in decade per 100 mv. As the threshold voltage continues to drop, the leakage current begins to become a substantial factor in current consumption, compared with the operating current. Since the operating current continues to drop as Moore's law while the leakage current continues to increase as scaling down continues its course.

Accordingly, it is desirable to develop methods and apparatus to reduce the leakage current without noticeable impact on the performance of the device.

BRIEF SUMMARY OF THE INVENTION

Method and apparatus of imaging gastrointestinal tract by using a capsule endoscope are disclosed. According to this method, at least two operating states during a course of gastrointestinal examination using the capsule endoscope are determined, wherein said at least two operating states comprise a first operating state and a second operating state, and the capsule endoscope comprises one or more capsule processors equipped with a back bias control. In response to a current operating state being the first operating state or the second operating state, the current body biasing for said one or more capsule processors is set to a first body biasing or a second body biasing accordingly, wherein the first body biasing is different from the second body biasing. One or more images are captured using the current body biasing for said one or more capsule processors.

In one embodiment, the first operating state corresponds to the capsule endoscope in esophagus or prior to reaching the esophagus, and the second operating state corresponds to the capsule endoscope in a part of human gastrointestinal distal to the esophagus. In one embodiment, the capsule endoscope is set to the first operating state during an initial period of time after the capsule endoscope is turned on. In one embodiment, the initial period of time is less than 2 minutes. In one embodiment, the capsule endoscope is set to the first operating state after the capsule endoscope is detected in vivo. In one embodiment, the capsule endoscope is set to the first operating state within 2 minutes after the capsule endoscope is detected in vivo. In another embodiment, the first body biasing is more forward back biased or less reverse back biased than the second body biasing. In another embodiment, the capsule endoscope enters the first state after detecting the capsule endoscope entering the human body. There are various ways to detect that the capsule endoscope enters the human body. For example, the detection can be based on the image sensor pixel values, such as the pixel values becoming much smaller. Before entering the first state, the back bias can be set to be less forward or more reverse relative to the first state.

In one embodiment, the first operating state corresponds to a fast frame rate operation and the second operating state corresponds to a regular frame rate operation. In one embodiment, the first body biasing is more forward back biased or less reverse back biased than the second body biasing.

In one embodiment, the first operating state corresponds to a high definition operation and the second operating state corresponds to a regular definition operation. In one embodiment, the first body biasing is more forward back biased or less reverse back biased than the second body biasing.

BRIEF DESCRIPTION OF THE DRAWINGS

FIG. 3 illustrates an example fully depleted silicon on insulator (FD-SOI) transistor, where the device includes a layer of ultra-thin buried oxide.

FIG. 4A shows an example of the device structure for a forward body bias (FBB).

FIG. 4B shows an example of the device structure for a reverse body bias (RBB).

DETAILED DESCRIPTION OF THE INVENTION

Figure 1:
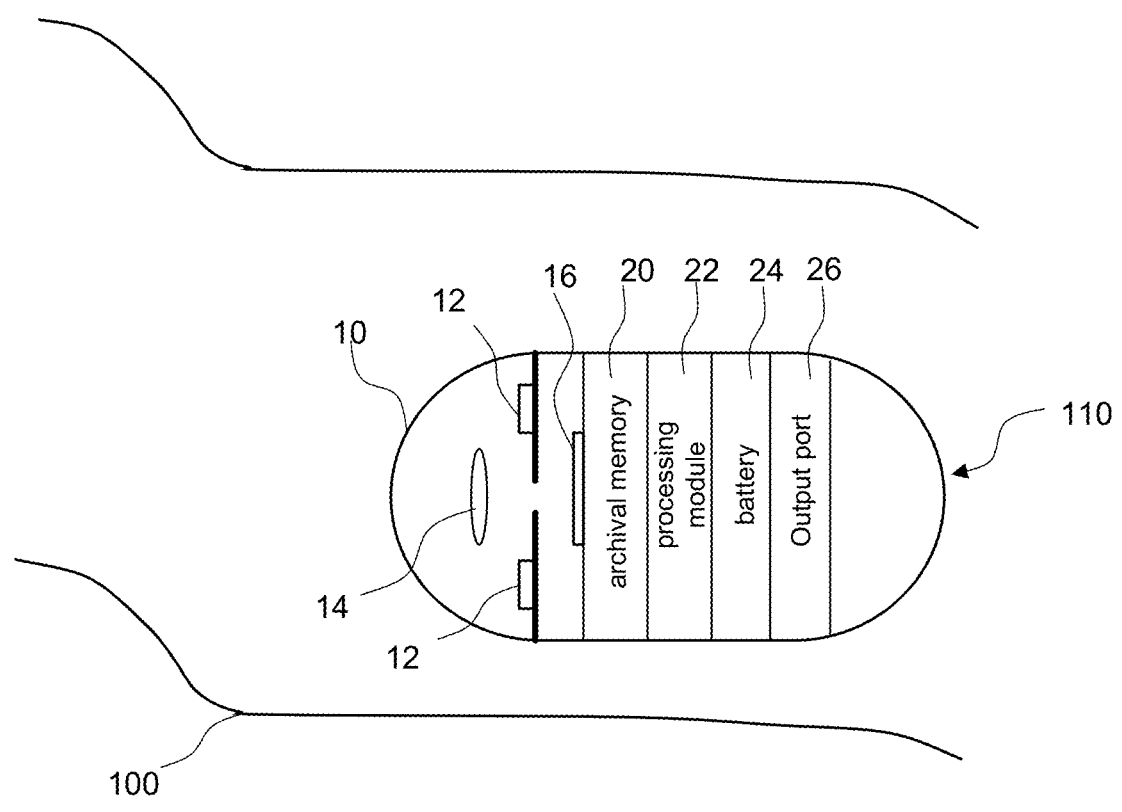
FIG. 1 illustrates an exemplary capsule endoscope with one or more capsule processors.
Figure 2:
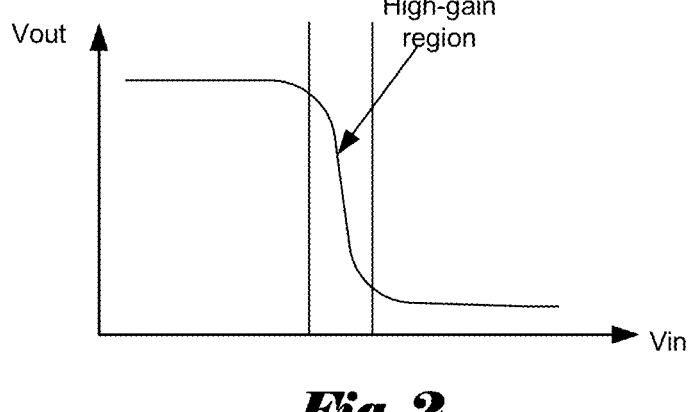
FIG. 2 illustrates an example of transfer curve for an inverter.

It will be readily understood that the components of the present invention, as generally described and illustrated in the figure herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawing, wherein like parts are designated by like numerals throughout. The following description is intended only by way of example, and simply illustrates certain selected embodiments of apparatus and methods that are consistent with the invention as claimed herein.

In the field of semiconductor technology, various leakage control schemes have been developed. One example of device structure for transistors below 30 nm, is a fully depleted silicon on insulator (FD-SOI) transistor. FIG. 3 illustrates an example of FD-SOI transistor, where the device includes a layer of ultra-thin buried oxide. The buried oxide layer lowers the parasitic capacitance between the source and the drain. It also efficiently confines the electrons flowing from the source to the drain, dramatically reducing performance-degrading leakage currents. A body bias contact 310 is provided for applying a biasing voltage. The body bias is often referred as back bias in the semiconductor field. Therefore, both body bias and back bias are used interchangeably in this disclosure.

FIG. 4A shows an example of the device structure for a forward body bias (FBB) and FIG. 4B shows an example of the device structure for a reverse body bias (RBB). There are other device structures used below 20-30 nm. When the body effect is biased in the more forward direction, the transistor source drain conduction current will increase, which increases the speed and performance bandwidth. For FBB, its leakage current will also increase, which is the current dissipated, but does not increase speed or performance bandwidth. When the body effect is biased in the opposite direction (i.e., RBB), the transistor source drain conduction current will decrease, but decreases speed and performance bandwidth as well, while its leakage current will also decrease.

Accordingly, the use of body biasing control can provide dynamic leakage reduction and performance control. Therefore, depending on the performance requirement, a proper biasing voltage can be applied to achieve the desired performance and leakage current reduction.

For an endoscopic capsule operation, esophagus needs much higher bandwidth, due to the fast transit time in esophagus than the rest of GI tract. To increase the speed and bandwidth, the integrated circuit has the advantage of dealing with fast frame rate by biasing it in more forward back bias (or less reverse bias) at the expense of higher leakage current. However, the esophagus transit time normally is less than 1 minute while the rest of the transit time in GI takes hours. The total energy (i.e., power×duration) dissipation due to the leakage current during the esophagus transit time is negligible. During the rest of the GI transit time, we may use less forward (or more reverse) back bias to reduce the leakage current for very long transit time where the frame rate requirement is much lower.

Occasionally, it may be desirable to examine stomach with fast frame rate for a limited duration of time. Therefore, more forward bias (or less reverse) can be applied during the stomach examination, and the less forward back bias (or more reverse back bias) can be adopted afterword. In another embodiment, when the capsule system detects fast motion in the rest of the GI tract, more forward back bias can be applied until the detected fast motion finishes, and then the less forward back bias (or more reverse back bias) can be adopted.

In one embodiment, when capsule transit is at the substantial beginning period of duration in vivo (e.g., the first 1 or 2 minutes), more forward back bias is applied, and after this period of time, less forward back bias or no forward back bias is applied. In another embodiment, when capsule transit is at the substantial beginning period of duration in vivo (e.g., the first 1 or 2 minutes), no or less reverse back bias is applied, and substantial during the duration after this period of time, more reverse back bias is applied.

In one embodiment, when fast frame rate or high definition image capture, both requiring high bandwidth performance, is required, more forward back bias is applied. When the bandwidth requirement is less, less forward back bias or no forward back bias is applied. In another embodiment, when fast frame rate or high definition, both requiring high bandwidth performance, is required, no back bias or less reverse back bias is applied, and when the bandwidth requirement is less, more reverse back bias is applied.

In one embodiment, when fast frame rate or high definition image capture, both requiring high bandwidth performance, is required, more forward back bias is applied. When the bandwidth requirement is less, less forward back bias or no forward back bias or even reverse back bias is applied. In another embodiment, when fast frame rate or high definition image capture, both requiring high bandwidth performance, is required, forward bias or no back bias or less reverse back bias is applied. When the bandwidth requirement is less, more reverse back bias is applied.

The capsule endoscope may also be configured to have a low frame rate. This state will be useful when there is no need to capture images at a normal or regular frame rate (e.g. 2-5 frames per second). For example, occasionally the capsule endoscope may get stuck in the GI tract and has no or little motion for a period of time. Therefore, a slow frame rate may help to extend the battery life of the capsule endoscope. The low frame rate can be achieved by more reverse back bias to lower the leakage current compared to the state corresponding to regular frame rate.

During the course of GI imaging by the capsule endoscope, the capsule endoscope is operated at a regular frame rate for most of the time. The regular state can be achieved by setting the back bias to a default level. In case that a faster frame rate is needed, the back bias can be set to more forward back biasing or less backward back biasing (if reverse back biasing being used in the regular state already). In case that a slower frame rate is needed, the back bias can be set to more reverse back biasing or less forward back biasing (if forward back biasing being used in the regular state already).

In the above disclosure, the preferred embodiments rely said one or more capsule processors inside the capsule endoscope via a control scheme. The control decision can be implemented based on said one or more processors. Nevertheless, the control decision may also be made outside the capsule endoscope. For example, in the case that the capsule endoscope comprises a wireless transmitter (e.g. a transmitter using RF (Radio Frequency) signal) to transmit the captured images to a wireless receiver outside the human body. In this case, control decision can be made based on the images received using a computer, a workstation or any device with sufficient computational capability. The control decision can be send wirelessly to the capsule endoscope to adjust the back bias accordingly.

The external control scheme mentioned above can be implemented using various programmable devices such as micro-controller, central processing unit (CPU), field programmable gate array (FPGA), digital signal processor (DSP) or any programmable processor with or without firmware or software. The external scheme may have AI to detect different anatomy (e.g. stomach) and send the command wirelessly to the capsule to adjust the back bias accordingly.

Figure 5:
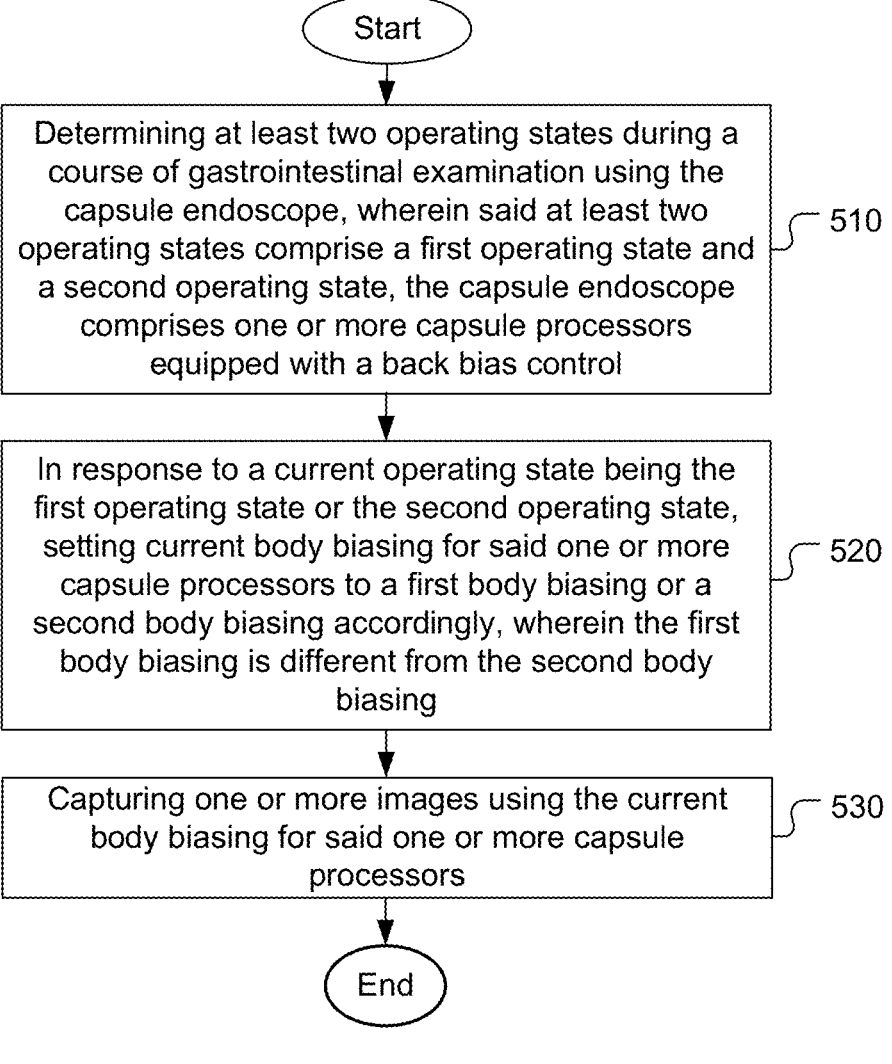
FIG. 5 illustrates an exemplary flowchart for capturing in vivo images using a capsule endoscope with back bias control according to an embodiment of the present invention.

FIG. 5 illustrates an exemplary flowchart for capturing in vivo images using a capsule endoscope with back bias control according to an embodiment of the present invention. According to this method, at least two operating states during a course of gastrointestinal examination using a capsule endoscope are determined in step 510, wherein said at least two operating states comprise a first operating state and a second operating state, and the capsule endoscope comprises one or more capsule processors equipped with a back bias control. In response to a current operating state being the first operating state or the second operating state, current body biasing is set for said one or more capsule processors to a first body biasing or a second body biasing accordingly in step 520, wherein the first body biasing is different from the second body biasing. One or more images are captured using the current body biasing for said one or more capsule processors in step 530.

The above description is presented to enable a person of ordinary skill in the art to practice the present invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of imaging gastrointestinal tract by using a capsule endoscope, the method comprising:

determining at least two operating states during a course of gastrointestinal examination using the capsule endoscope, wherein said at least two operating states comprise a first operating state and a second operating state, the capsule endoscope comprises one or more capsule processors equipped with a back bias control;

in response to a current operating state being the first operating state or the second operating state, setting current body biasing for said one or more capsule processors to a first body biasing or a second body biasing accordingly, wherein the first body biasing is different from the second body biasing; and capturing one or more images using the current body biasing for said one or more capsule processors, and wherein the first operating state corresponds to the capsule endoscope in esophagus or prior to reaching the esophagus, and the second operating state corresponds to the capsule endoscope in a part of human gastrointestinal distal to the esophagus.

2. The method of claim 1, wherein the capsule endoscope is set to the first operating state during an initial period of time after the capsule endoscope is turned on.

3. The method of claim 2, wherein the initial period of time is less than 2 minutes.

4. The method of claim 1, wherein the capsule endoscope is set to the first operating state after the capsule endoscope is detected in vivo.

5. The method of claim 4, wherein the capsule endoscope is set to the first operating state within 2 minutes after the capsule endoscope is detected in vivo.

6. A method of imaging gastrointestinal tract by using a capsule endoscope, the method comprising:

determining at least two operating states during a course of gastrointestinal examination using the capsule endoscope, wherein said at least two operating states comprise a first operating state and a second operating state, the capsule endoscope comprises one or more capsule processors equipped with a back bias control;

in response to a current operating state being the first operating state or the second operating state, setting current body biasing for said one or more capsule processors to a first body biasing or a second body biasing accordingly, wherein the first body biasing is different from the second body biasing; and capturing one or more images using the current body biasing for said one or more capsule processors, and wherein the first operating state corresponds to a fast frame rate operation and the second operating state corresponds to a regular frame rate operation.

7. The method of claim 6, wherein the first body biasing is more forward back biased or less reverse back biased than the second body biasing.

8. A method of imaging gastrointestinal tract by using a capsule endoscope, the method comprising:

determining at least two operating states during a course of gastrointestinal examination using the capsule endoscope, wherein said at least two operating states comprise a first operating state and a second operating state, the capsule endoscope comprises one or more capsule processors equipped with a back bias control;

in response to a current operating state being the first operating state or the second operating state, setting current body biasing for said one or more capsule processors to a first body biasing or a second body biasing accordingly, wherein the first body biasing is different from the second body biasing; and capturing one or more images using the current body biasing for said one or more capsule processors, and wherein the first operating state corresponds to a high definition operation and the second operating state corresponds to a regular definition operation.

9. The method of claim 8, wherein the first body biasing is more forward back biased or less reverse back biased than the second body biasing.

10. A non-transitory computer-readable medium having stored thereon a computer-readable code executable by a processor to cause the processor to:

determine at least two operating states during a course of gastrointestinal examination using a capsule endoscope, wherein said at least two operating states comprise a first operating state and a second operating state, and the capsule endoscope comprises one or more capsule processors equipped with a back bias control;

in response to a current operating state being the first operating state or the second operating state, set current body biasing for said one or more capsule processors to a first body biasing or a second body biasing accordingly, wherein the first body biasing is different from the second body biasing; and capture one or more images using the current body biasing for said one or more capsule processors, and wherein the first operating state corresponds to the capsule endoscope in esophagus or prior to reaching the esophagus, and the second operating state corresponds to the capsule endoscope in a part of human gastrointestinal distal to the esophagus.

11. A capsule endoscope for capturing in vivo images, comprising:

an image sensor to capture images;

a light source to provide illumination for the image sensor;

one or more capsule processors equipped with a back bias control;

a battery to provide power to the image sensor, the light source and said one or more capsule processors; and a capsule housing adapted to be swallowed, wherein the image sensor the light source, said one or more capsule processors and the battery are enclosed in the capsule housing;

wherein the image sensor, the light source and said one or more capsule processors are configured to:

determine at least two operating states during a course of gastrointestinal examination using the capsule endoscope, wherein said at least two operating states comprise a first operating state and a second operating state;

in response to a current operating state being the first operating state or the second operating state, set current body biasing for said one or more capsule processors to a first body biasing or a second body biasing accordingly, wherein the first body biasing is different from the second body biasing; and capture one or more images using the current body biasing for said one or more capsule processors, and wherein the first operating state corresponds to the capsule endoscope in esophagus or prior to reaching the esophagus, and the second operating state corresponds to the capsule endoscope in a part of human gastrointestinal distal to the esophagus.

12. A capsule endoscope for capturing in vivo images, comprising:

an image sensor to capture images;

a light source to provide illumination for the image sensor;

one or more capsule processors equipped with a back bias control;

a battery to provide power to the image sensor, the light source and said one or more capsule processors; and

a capsule housing adapted to be swallowed, wherein the image sensor the light source, said one or more capsule processors and the battery are enclosed in the capsule housing;

wherein the image sensor, the light source and said one or more capsule processors are configured to:

determine at least two operating states during a course of gastrointestinal examination using the capsule endoscope, wherein said at least two operating states comprise a first operating state and a second operating state;

in response to a current operating state being the first operating state or the second operating state, set current body biasing for said one or more capsule processors to a first body biasing or a second body biasing accordingly, wherein the first body biasing is different from the second body biasing; and capture one or more images using the current body biasing for said one or more capsule processors, and wherein the first operating state corresponds to a fast frame rate operation and the second operating state corresponds to a regular frame rate operation.

13. A capsule endoscope for capturing in vivo images, comprising:

an image sensor to capture images;

a light source to provide illumination for the image sensor;

one or more capsule processors equipped with a back bias control;

a battery to provide power to the image sensor, the light source and said one or more capsule processors; and a capsule housing adapted to be swallowed, wherein the image sensor the light source, said one or more capsule processors and the battery are enclosed in the capsule housing;

wherein the image sensor, the light source and said one or more capsule processors are configured to:

determine at least two operating states during a course of gastrointestinal examination using the capsule endoscope, wherein said at least two operating states comprise a first operating state and a second operating state;

in response to a current operating state being the first operating state or the second operating state, set current body biasing for said one or more capsule processors to a first body biasing or a second body biasing accordingly, wherein the first body biasing is different from the second body biasing; and capture one or more images using the current body biasing for said one or more capsule processors, and wherein the first operating state corresponds to a high definition operation and the second operating state corresponds to a regular definition operation.

* * * * *